United States Patent
Vickery

(10) Patent No.: US 10,624,793 B2
(45) Date of Patent: Apr. 21, 2020

(54) TARGETED DRUG DELIVERY PAD

(71) Applicant: Dentmed Limited, Bristol (GB)

(72) Inventor: Ian Malcolm Vickery, Bristol (GB)

(73) Assignee: DENTMED LIMITED, Bristol (GB)

( * ) Notice: Subject to any disclaimer, the term of this patent is extended or adjusted under 35 U.S.C. 154(b) by 0 days.

(21) Appl. No.: 15/992,710

(22) Filed: May 30, 2018

(65) Prior Publication Data
US 2019/0015257 A1    Jan. 17, 2019

(30) Foreign Application Priority Data
Jul. 13, 2017  (GB) .................. 1711271.5

(51) Int. Cl.
| A61F 13/00 | (2006.01) |
| A61M 35/00 | (2006.01) |
| A61K 9/70 | (2006.01) |
| A61F 13/45 | (2006.01) |
| A61F 13/53 | (2006.01) |

(52) U.S. Cl.
CPC .. *A61F 13/00068* (2013.01); *A61F 13/00063* (2013.01); *A61K 9/7023* (2013.01); *A61M 35/00* (2013.01); *A61F 2013/4506* (2013.01); *A61F 2013/530839* (2013.01); *A61M 2207/10* (2013.01)

(58) Field of Classification Search
CPC .......... A61F 13/00068; A61F 13/00063; A61F 2013/4506; A61F 2013/530839; A61F 13/00012; A61F 13/00008; A61F 13/00017; A61M 35/00; A61M 2207/10; A61K 9/7023

USPC ......................................... 604/305
See application file for complete search history.

(56) References Cited

U.S. PATENT DOCUMENTS

| 5,254,346 A | * | 10/1993 | Tucker | ................. A61K 9/7084 424/434 |
| 5,662,925 A | * | 9/1997 | Ebert | ..................... A61K 9/703 424/447 |
| 5,770,220 A | * | 6/1998 | Meconi | ................ A61K 9/7084 424/448 |

(Continued)

FOREIGN PATENT DOCUMENTS

WO    2005053641 A1    6/2005

OTHER PUBLICATIONS

Examination Report in corresponding British Patent Application No. GB1711271.5 dated Jan. 22, 2018. 3 pages.
(Continued)

*Primary Examiner* — Catherine L Anderson
*Assistant Examiner* — Gabriella E Burnette
(74) *Attorney, Agent, or Firm* — Leason Ellis LLP

(57) ABSTRACT

An article 1 comprises a hydrophilic foam layer 3; a reservoir cover 5 in contact with a first main surface of the hydrophilic foam layer 3, the reservoir cover 5 enclosing a reservoir cavity 7 together with the first main surface of the hydrophilic foam layer 3, the reservoir cavity 7 being for containing a fluid; and a hydrophobic foam layer 9 formed over the first main surface of the hydrophilic foam layer 3 and the reservoir cover 5. Fluid can be dispensed from the reservoir cavity 7 through a lower surface of the hydrophilic foam layer 3 by pressing on the hydrophobic foam layer 9 so that the reservoir cover 5 is compressed.

13 Claims, 4 Drawing Sheets

(56) References Cited

U.S. PATENT DOCUMENTS

| | | | | |
|---|---|---|---|---|
| 6,328,992 B1* | 12/2001 | Brooke | ............... | A61K 9/7061 |
| | | | | 424/443 |
| 9,168,180 B2* | 10/2015 | Ha | ....................... | A61F 13/025 |
| 10,245,186 B2* | 4/2019 | Olson | ............... | A61F 13/00987 |
| 2004/0078016 A1* | 4/2004 | Baker | ............... | A61F 13/15203 |
| | | | | 604/378 |
| 2005/0266061 A1* | 12/2005 | Stinchcomb | ......... | A61K 9/0014 |
| | | | | 424/448 |
| 2010/0286639 A1* | 11/2010 | Scholz | ................ | A61M 1/0088 |
| | | | | 604/319 |
| 2011/0117208 A1* | 5/2011 | Richardson | ............ | A61K 33/42 |
| | | | | 424/606 |
| 2016/0199313 A1* | 7/2016 | LeDonne | ............. | A61K 31/485 |
| | | | | 604/290 |

OTHER PUBLICATIONS

Search Report in corresponding British Patent Application No. GB1711271.5 dated Nov. 8, 2017. 3 pages.

* cited by examiner

TARGETED DRUG DELIVERY PAD

CROSS-REFERENCE TO RELATED PATENT APPLICATIONS

The present application claims priority under 35 U.S.C. § 119 to GB Patent Application No. 1711271.5, filed Jul. 13, 2017, which is hereby incorporated by reference in its entirety.

FIELD OF THE INVENTION

The present invention relates to an article. More specifically, the present invention relates to an article for applying a fluid, such as an analgesic fluid, on a surface of a person, such as the skin of the person.

BACKGROUND OF THE INVENTION

Acute or chronic pain in patients can be treated with analgesic medicines. Such medicines can be taken orally, injected, or applied topically to the person's skin.

It can also be advantageous to deliver other types of medication topically, for example to provide localised delivery of the medication and to provide delivery of the medication over a longer period of time.

It is known from GB2517092 to apply a fluid medicament to the skin of a person using a polyurethane foam article comprising a hydrophobic polyurethane foam layer and a hydrophilic/haemophilic polyurethane foam layer. The article has at least one cavity therein, at the interface between the hydrophobic polyurethane foam layer and the hydrophilic/haemophilic polyurethane foam layer. The cavity can be filled with a fluid medicament, typically a fluid analgesic, once the article is firmly positioned in the correct anatomical selected position.

In use, the fluid medicament should be absorbed into the hydrophilic/haemophilic polyurethane foam layer, which is placed into contact with the skin of a patient. The fluid medicament will therefore be applied to the skin of the patient. The amount of fluid medicament applied to the skin of the patient can be increased by applying pressure to the hydrophobic polyurethane foam layer, typically by a physician, nurse or the patient pressing on the hydrophobic polyurethane foam layer. The hydrophobic polyurethane foam layer prevents flow of the fluid medicament away from the skin of the patient, so that when the hydrophobic polyurethane foam layer is pressed, the fluid medicament is caused to be displaced from the cavity towards the skin of the patient through the hydrophilic/haemophilic polyurethane foam layer, so that the fluid medicament is released from the article and applied to the skin of the patient.

In this manner, a fluid medicament should be applied to the patient's skin from the hydrophilic/haemophilic polyurethane foam layer.

In GB2517092 the cavity or cavities for containing the fluid medicament are formed by using one or more metal tongues. Specifically, during manufacture of the article in a mould, one or more metal tongues are positioned on top of the hydrophilic/haemophilic polyurethane foam layer to hold the hydrophilic/haemophilic polyurethane foam layer in position in the mould. The one or more metal tongues protrude from the inside of the mould to the outside of the mould. The hydrophobic polyurethane foam layer is then formed over the hydrophilic/haemophilic polyurethane foam layer and the one or more metal tongues in the mould. Once the polymerisation process has been completed, the metal tongue or tongues are removed from the resulting article. This has the effect of forming one or more cavities in the article, with the number of cavities corresponding to the number of metal tongues used. The removal of the metal tongue or tongues also means that any such cavity has a vent extending from it to the exterior of the article. The cavity or cavities can then be filled with a fluid medicament via the corresponding vent, and then the vent sealed to seal the fluid medicament in the cavity or cavities.

The present inventor has realised that the foam article disclosed in GB2517092 can be improved, to improve the application of the fluid medicament to the surface of a patient (e.g. the patient's skin), i.e. to improve targeted drug delivery using the article.

SUMMARY OF THE INVENTION

In particular, the present inventor has realised that during the manufacture of the article disclosed in GB2517092, in some circumstances a skin layer that is substantially impermeable to fluid can be formed on the surface of the hydrophilic/haemophilic polyurethane foam layer under the metal tongues.

More specifically, during the manufacture of the article disclosed in GB2517092, it is possible in some circumstances for some of the hydrophobic polyurethane foam material to penetrate beneath the one or more metal tongues, so that a skin of hydrophobic polyurethane foam is formed over the upper surface of the hydrophilic/haemophilic polyurethane foam layer beneath the one or more metal tongues.

This is believed to occur because penetration of the hydrophobic polyurethane foam material into the upper surface of the hydrophilic/haemophilic polyurethane foam layer can cause some distortion of the upper surface of the hydrophilic/haemophilic polyurethane foam layer during the manufacture of the article.

In these circumstances, when the one of more metal tongues are removed to produce the one or more cavities for containing a liquid, a skin layer of hydrophobic polyurethane foam that is impermeable to the liquid may be formed at the bottom of the one or more cavities, so that the liquid is unable to pass through the bottom of the one or more cavities to enter into the hydrophilic/haemophilic polyurethane foam layer.

Therefore, this problem can prevent the fluid medicament from being applied to the patient's skin during use of the article.

The present invention overcomes this problem and thereby correctly achieves application of the fluid medicament to the patient's skin.

At its most general, the present invention proposes providing a reservoir cover in contact with an upper surface of a hydrophilic/haemophilic foam layer, so that the reservoir cover encloses a cavity together with the upper surface of the hydrophilic/haemophilic foam layer. By pressing the reservoir cover towards the hydrophilic/haemophilic foam layer while a hydrophobic foam layer is formed over the upper surface of the hydrophilic/haemophilic foam layer and the reservoir cover, the reservoir cover can remain in tight contact with the upper surface of the hydrophilic/haemophilic foam layer, so that hydrophobic foam material is prevented from penetrating into the cavity beneath the reservoir cover. Thus, the formation of a skin of hydrophobic foam that is substantially impermeable to fluid flow directly underneath the cavity is prevented, and the application of the fluid medicament to the patient's skin is therefore correctly achieved.

According to a first aspect of the present invention there is provided an article comprising:

a hydrophilic foam layer;

a reservoir cover in contact with a first main surface of the hydrophilic foam layer, the reservoir cover enclosing a reservoir cavity together with the first main surface of the hydrophilic foam layer, the reservoir cavity being for containing a fluid; and a hydrophobic foam layer formed over the first main surface of the hydrophilic foam layer and the reservoir cover.

According to the first aspect of the present invention, the reservoir cavity is formed between the reservoir cover and the first main surface of the hydrophilic foam layer, and the reservoir cover is in contact with the first main surface of the hydrophilic foam layer to enclose the reservoir cavity. This means that no skin layer of hydrophobic foam that is substantially impermeable to the fluid that the reservoir cavity is intended to contain is formed at the bottom surface of the reservoir cavity. Thus, in use of the article, fluid is able to readily pass from the reservoir cavity through the bottom surface of the reservoir cavity towards the surface with which the article is in contact through the hydrophilic foam layer.

Therefore, the application of a fluid medicament contained in the reservoir cavity on a patient's skin is improved by the present invention.

The term "hydrophilic" may additionally or alternatively mean haemophilic.

The term "hydrophilic" as used in this application may merely mean a foam that is absorbent of water or other fluids such as blood.

The term "hydrophobic" as used in this application may merely mean a form that is not absorbent of water or other fluids such as blood.

The term "enclosing" may alternatively be replaced with one of the following terms: surrounding, bordering, bounding, or defining.

The reservoir cover is distinct from the hydrophilic foam layer and the hydrophobic foam layer. In particular, the reservoir cover is formed separately to the hydrophilic foam layer and the hydrophobic foam layer and from a different material.

The reservoir cavity may alternatively be called a reservoir space, a reservoir void, a reservoir volume, or a reservoir hollow.

In the present invention, the first main surface of the hydrophilic foam layer forms one boundary, edge or surface of the reservoir cavity. The reservoir cover forms the other boundary/boundaries, edge(s) or surface(s) of the reservoir cavity. The reservoir cavity therefore forms a space or gap between the first main surface of the hydrophilic foam layer and the reservoir cover that is enclosed between the first main surface of the hydrophilic foam layer and the reservoir cover. The reservoir cover covers the reservoir cavity (when viewed from above).

The reservoir cover may alternatively be called a reservoir shell, a reservoir casing, a reservoir housing or a reservoir part.

The reservoir cavity will be empty prior to the delivery of a pharmaceutical fluid. The term "empty" does not exclude the reservoir cavity containing air. Typically a pharmaceutical fluid will be supplied into the reservoir cavity when the article is positioned on the patient in the selected site.

The first main surface of the hydrophilic foam layer can be considered to be an upper surface of the hydrophilic foam layer, and another opposite main surface of the hydrophilic foam layer can be considered to be a bottom surface of the hydrophilic foam layer.

In use of the article, the bottom surface of the hydrophilic foam layer is positioned on or proximal to the surface on which the fluid is to be applied, typically the skin of a patient.

The hydrophilic foam layer and/or the hydrophobic foam layer are typically substantially planer. For example, they may be sheet-like layers, or slabs.

The reservoir cover is substantially impermeable to the fluid that is intended to be contained in the reservoir cavity. Thus, the fluid in the reservoir cavity is prevented from passing through the reservoir cover.

Since the hydrophilic foam layer and the hydrophobic foam layer are formed of foam, both of these layers are compressible. This facilitates compression of the article to apply the fluid on the surface.

The reservoir cover is also flexible/compressible, so that it can be depressed or compressed by a person's fingers. This means that the patient can manually reduce the size of the reservoir cavity, thereby displacing fluid from the reservoir cavity into the hydrophilic foam layer, by pressing on the hydrophobic foam layer so that the reservoir cover is compressed. However, the reservoir cover preferably returns to its original shape when it is no longer being pressed. In other words, the reservoir cover preferably behaves elastically rather than plastically.

When the hydrophobic foam layer is formed over the hydrophilic foam layer, some of the hydrophobic foam penetrates into the first main surface of the hydrophilic foam layer. This bonds the hydrophobic foam layer and the hydrophilic foam layer together, so that a good bond or seal is formed between them. This can create an air-tight enclosure around the reservoir cover.

The first aspect of the present invention may comprise one, or, to the extent that they are compatible, any combination of the following optional features.

The article may be an article for applying a fluid on a surface of a person, for example the skin of a person.

The article may be a pad.

The article may further comprising a fluid conduit connected to the reservoir cavity for supplying fluid into the reservoir cavity. For example, an end of the fluid conduit may be connected to an inner surface of the reservoir cover inside the reservoir cavity. Being connected to the reservoir cavity means that the fluid conduit is in fluid communication with the reservoir cavity. In other words, the fluid conduit is able to supply fluid into the reservoir cavity.

The fluid conduit may be a catheter.

An edge or edges of the reservoir cover in contact with the first main surface of the hydrophilic foam layer may be penetrated into the first main surface of the hydrophilic foam layer. In that case, preferably all of the edges of the reservoir cover that are in contact with the first main surface of the hydrophilic foam layer are penetrated into the first main surface of the hydrophilic foam layer. This forms a tight seal between the reservoir cover and the hydrophilic foam layer that prevents any of the hydrophobic foam material from penetrating into the reservoir cavity beneath the reservoir cavity. Being penetrated into the first main surface of the hydrophilic foam layer means that the edge or edges of the reservoir cover protrude or extend beyond the first main surface of the hydrophilic foam layer into (inside) the hydrophilic foam layer.

The reservoir cover may be made from a polymer.

The reservoir cover may be made from polyvinyl chloride (PVC). In that case, preferably the polyvinyl chloride includes a medically acceptable blowing agent.

The hydrophobic foam layer may be further formed on side surfaces of the hydrophilic foam layer. In this case, the hydrophobic foam layer is preferably formed on all side surfaces of the hydrophilic foam layer (in other words all surfaces of the hydrophilic foam layer except for the upper and lower surfaces of the hydrophilic foam layer). This prevents the fluid from being able to escape from the article through the side surfaces of the hydrophilic foam layer, so that the fluid can only be dispensed from the article through the bottom surface of the article that is in contact with the patient.

A main side of the reservoir cover opposite to the first main surface of the hydrophilic foam layer may have a substantially rectangular shape. In other words, the reservoir cover may have a rectangular shape when viewed in plan view (from above).

The main side of the reservoir cover may be a square with a side length of between 2 and 10 centimetres.

A main side of the reservoir cover opposite to the first main surface of the hydrophilic foam layer may have a thickness of between 150 μm and 250 μm. This thickness means that the reservoir cover is suitably flexible/compressible. Indeed, all sides of the reservoir cover may have a thickness of between 150 μm and 250 μm. A preferred thickness for the reservoir cover may be 200 μm.

The reservoir cavity may have a volume of between 2 and 40 millilitres. In other words, the maximum volume of fluid that the reservoir cavity is capable of containing may be between 2 and 40 millilitres. Preferred maximum volumes may be between 4 and 36 mm.

The reservoir cover may have one or more side walls in contact with the first main surface of the hydrophilic foam layer, wherein the one or more side walls are inclined relative to a normal line of the first main surface. Where the reservoir cover has a rectangular shape when viewed from above, the reservoir cover has four side walls.

Angling the side walls of the reservoir cover with respect to the surface of the hydrophilic foam layer may aid the compressibility of the reservoir cover, and may also ensure that the fluid in the reservoir cavity is only distributed in the hydrophilic foam layer.

The one or more side walls may be at an angle of between 30 degrees and 60 degrees to the normal line of the first main surface. A preferred angle may be 45 degrees.

The article may comprise a tape in contact with an outer surface of the reservoir cover, the tape protruding from at least one side surface of the article. The tape aids in attaching the article to a surface, for example the skin of a patient, a limb bandage, or underwear.

Typically the tape will protrude from two opposite side surfaces of the article. This aids in securely attaching the article to the surface.

The hydrophilic foam layer may comprise a hydrophilic polyurethane foam.

The hydrophilic foam layer may be made from a polyol and isocyanate composition, in which the weight ratio of polyol to isocyanate is from 1:1 to 1.5:1.

In the polyol and isocyanate composition that forms the hydrophilic foam layer: the polyol may comprise butane diol, benzenepropanoic acid, 3,5-bis[1,1-dimethylethyl]-4-hydroxy-C7-9 branched alkyl esters (wherein C7-9 is understood to be a carbon backbone having 7 to 9 carbon atoms in it), glycerine, silicone surfactants and triethylene diamine, and/or the isocyanate may comprise diphenylmethane-4,4-diisocyanate and triphenylphosphite.

The hydrophobic foam layer may comprise a hydrophobic polyurethane foam.

The hydrophobic foam layer may be made from a polyol and isocyanate composition in which the weight ratio of polyol to isocyanate is from 2:1 to 2.5:1.

In the polyol and isocyanate composition that forms the hydrophobic foam layer: the polyol may comprise 94.8% by weight polyoxyalkylene triols, 1.8% by weight triethanolamine, 0.2% by weight dipropylene glycol, 0.1% by weight triethyldiamine, 0.4% by weight organo-modified polysiloxanes, 2.1% by weight C9-11 alcohol ethoxylate and 0.6% by weight 2 [[2 dimethylamino)ethyl]methylamino] ethanol, and/or the isocyanate may comprise 50% to 77% by weight diphenylmethanediisocyanate, isomers and homologues thereof, and 23% to 50% by weight isocyanates that are the reaction product of the polyol with methylenediphenyl diisocyanate.

The article may comprise an analgesic fluid in the reservoir cavity. Thus, the article may be for applying an analgesic fluid to a surface of a person, to treat pain. Typically a fluid will be supplied into the reservoir cavity immediately before, or when, the article is positioned on the surface on which the fluid is to be provided.

According to a second aspect of the present invention there is provided a method of forming an article, the method comprising:

positioning a reservoir cover in contact with a first main surface of a hydrophilic foam layer, so that the reservoir cover encloses a reservoir cavity together with the first main surface of the hydrophilic foam layer, the reservoir cavity being for containing a fluid; and forming a hydrophobic foam layer over the first main surface of the hydrophilic foam layer and the reservoir cover;

wherein the method further comprises pressing the reservoir cover towards the first main surface of the hydrophilic foam layer when the hydrophobic foam layer is formed over the first main surface of the hydrophilic foam layer and the reservoir cover.

Pressing the reservoir cover towards the first main surface of the hydrophilic foam layer means that there is a tight seal between the reservoir cover and the first main surface of the hydrophilic foam layer. Thus, hydrophobic foam material is prevented from penetrating into the reservoir cavity under the reservoir cavity, so that no skin layer of hydrophobic foam is formed at the bottom of the cavity. For example, a liquid-proof, or air-tight seal may be formed between the reservoir cover and the first main surface of the hydrophobic foam layer.

Typically the hydrophilic foam layer will be prepared in advance.

The method according to the second aspect of the present invention may have any one of the optional features of the first aspect of the present invention discussed above, or any combination of these optional features.

Indeed, the method may be a method of forming an article according to the first aspect of the present invention discussed above, optionally including any one or more of the optional features of the article of the first aspect of the present invention discussed above.

The method according to the second aspect of the present invention may optionally have any one, or, to the extent that they are compatible, any combination of the following optional features.

Pressing the reservoir cover towards the first main surface of the hydrophobic foam layer may comprise using a pressure applying part to apply pressure to an outer surface of the reservoir cover.

The pressure applying part may comprise a plurality of rods or pins. Thus, the plurality of pins may contact an upper surface of the reservoir cover and apply pressure to the upper surface of the reservoir cover during manufacture of the article, thereby pushing the reservoir cover towards the hydrophilic foam layer. For example, where the reservoir cover has a rectangular shape in plan view, the pressure applying part may comprise four pins, and the four pins may be positioned to contact the upper surface of the reservoir cover at, or adjacent to, the corners of the upper surface of the reservoir cover.

The method may comprise forming the article using a mould. In other words, the hydrophobic foam layer may be formed (for example polymerised) inside a mould. Typically the hydrophilic foam layer will be produced separately, and therefore a suitably sized piece of hydrophilic foam will be positioned in the bottom of the mould when making the article.

In this case, the pressure applying part may be attached to an internal surface of a lid of the mould. Thus, when the lid of the mould is fitted to the remainder of the mould, the pressure applying part contacts and applies pressure to the upper surface of the reservoir cover that is positioned inside the mould in contact with the upper surface of the hydrophilic foam layer.

The pressing of the reservoir cover towards the first main surface of the hydrophilic foam layer may be sufficient to cause the edge or edges of the reservoir cover in contact with the first main surface of the hydrophilic foam layer to penetrate (dig, or protrude) into the first main surface of the hydrophilic foam layer.

As discussed above, this means that a fluid-tight or air-tight seal is formed between the reservoir cover and the hydrophilic foam layer, so that it is not possible for any of the hydrophobic foam material to penetrate into the reservoir cavity beneath the reservoir cover. A better seal will be formed where the reservoir cover digs into the hydrophilic foam layer instead of just being pressed into tight contact with the hydrophilic foam layer. However, an acceptable seal may be formed where the reservoir cover is just pressed into tight contact with the hydrophilic foam layer.

The method may comprise filling the reservoir cavity with an analgesic fluid. For example, as discussed above in relation to the first aspect of the present invention, the article may have a catheter in fluid communication with the reservoir cavity, and the method may comprise using the catheter to fill the reservoir cavity with analgesic fluid or other fluids. However, typically the reservoir cavity will only be filled with a suitable fluid immediately before, or during, use of the article on a patient. The article will therefore typically be manufactured and supplied without any fluid in the reservoir cavity.

The size of the hydrophilic foam layer in the mould may be marginally smaller than the size of the mould, to allow the hydrophobic layer to also be formed on side surfaces of the hydrophilic foam layer.

The method may include the steps of (i) disposing a non-polymerised hydrophobic layer comprising a polyol and isocyanate composition over a hydrophilic/haemophilic layer; and (ii) polymerising the hydrophobic layer.

In either aspect of the present invention, the fluid in the reservoir cavity may be e.g. bupivacaine, diclofenac or aspirin dissolved in a carrier. Of course, many other types of fluids could be used instead, so the present invention is not limited to any one particular type of fluid.

The term fluid may mean a liquid.

In either aspect of the present invention, either the hydrophilic foam layer or the hydrophobic foam layer may comprise barium sulphate, so that the article is visible in an x-ray image including the article.

BRIEF DESCRIPTION OF THE DRAWINGS

Embodiments of the present invention will now be discussed, by way of example only, with reference to the accompanying Figures, in which.

DETAILED DESCRIPTION OF THE PREFERRED EMBODIMENTS AND FURTHER OPTIONAL FEATURES OF THE INVENTION

Figure 1:
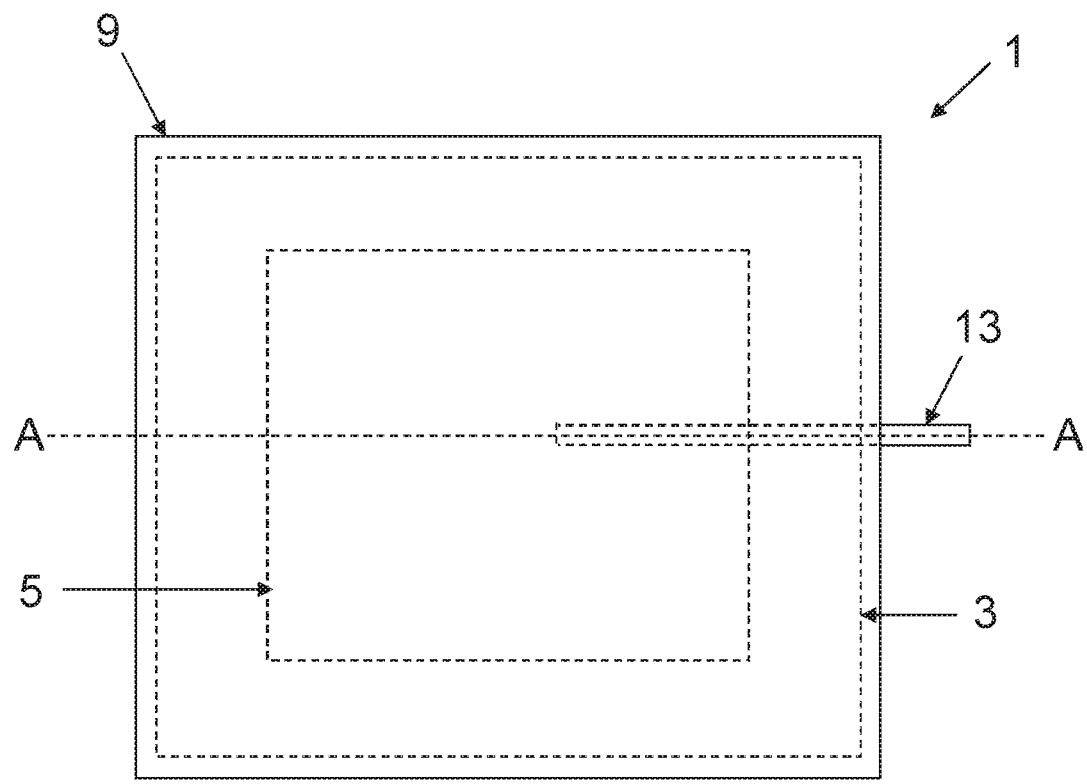
FIG. 1 is a plan view of an article according to an embodiment of the present invention.
Figure 2:
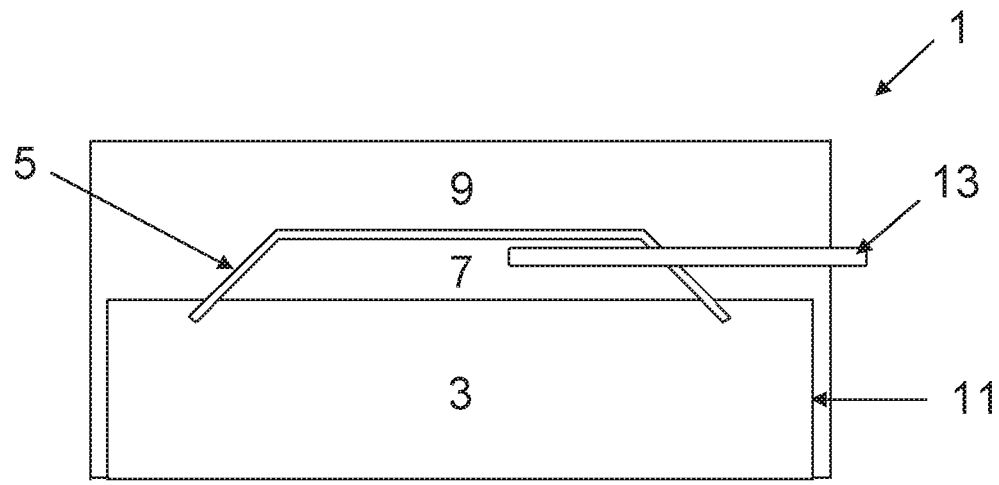
FIG. 2 is a cross-section view taken along the line A-A in FIG. 1.

An embodiment of the present invention is illustrated in FIGS. 1 and 2. As shown in these figures, the article 1 according to the embodiment of the present invention comprises a hydrophilic foam layer 3 as a lower layer thereof.

A reservoir cover 5 is positioned on top of an upper surface of the hydrophilic foam layer 3. The reservoir cover 5 encloses a reservoir cavity 7 together with the upper surface of the hydrophilic foam layer.

Lower edges of the reservoir cover 5 are penetrated into the hydrophilic foam layer 3 through the first main surface of the hydrophilic foam layer 3.

A hydrophobic foam layer 9 is formed over the upper surface of the hydrophilic foam layer 3 and over an upper surface of the reservoir cover 5. In addition, the hydrophobic foam layer 9 is formed over side surfaces 11 of the hydrophilic foam layer.

The reservoir cavity 7 is a space between the upper surface of the hydrophilic foam layer 3 and a lower surface of the reservoir cover 5. In use of the device 1, the reservoir cavity 7 is filled with a liquid intended to be provided on a surface of a person, for example a liquid analgesic medicine.

A fluid conduit 13 in the form of a catheter is provided passing from outside of the article 1, through the hydrophobic foam layer 9 and the reservoir cover 5, so that liquid can be supplied from the outside of the article 1 into the reservoir cavity 7. Typically the fluid conduit 13 will be fixed to an external surface of the reservoir cover 5. An advantage of fixing the fluid conduit 13 to an external surface of the reservoir cover 5 is that an adhesive used to fix the fluid conduit 13 to the external surface does not come into contact with the pharmaceutical fluid in the reservoir cavity 7. This will prevent any possible contamination of the pharmaceutical fluid by the adhesive, and for example may be important for regulatory reasons. For example, typically the reservoir cover 5 will have a channel passing through the reservoir cover 5 through which a tube of the fluid conduit 13 is passed in order for the fluid conduit 13 to be able to supply fluid into the reservoir cavity 7. In this case, the tube can be fixed to the external surface of the reservoir cover 5 just before the tube passes into the channel. Thus, when the hydrophobic foam polymerises over the reservoir cover 5 the adhered (e.g. glued) tube becomes entirely separated from any contact with the pharmaceutical fluid.

The catheter may be a silicone catheter.

Although not illustrated in the figures, some of the material of the hydrophobic foam layer 9 is penetrated into the upper portion of the hydrophilic foam layer 3. This bonds together the hydrophobic foam layer 9 and the hydrophilic foam layer 3.

Figure 3:
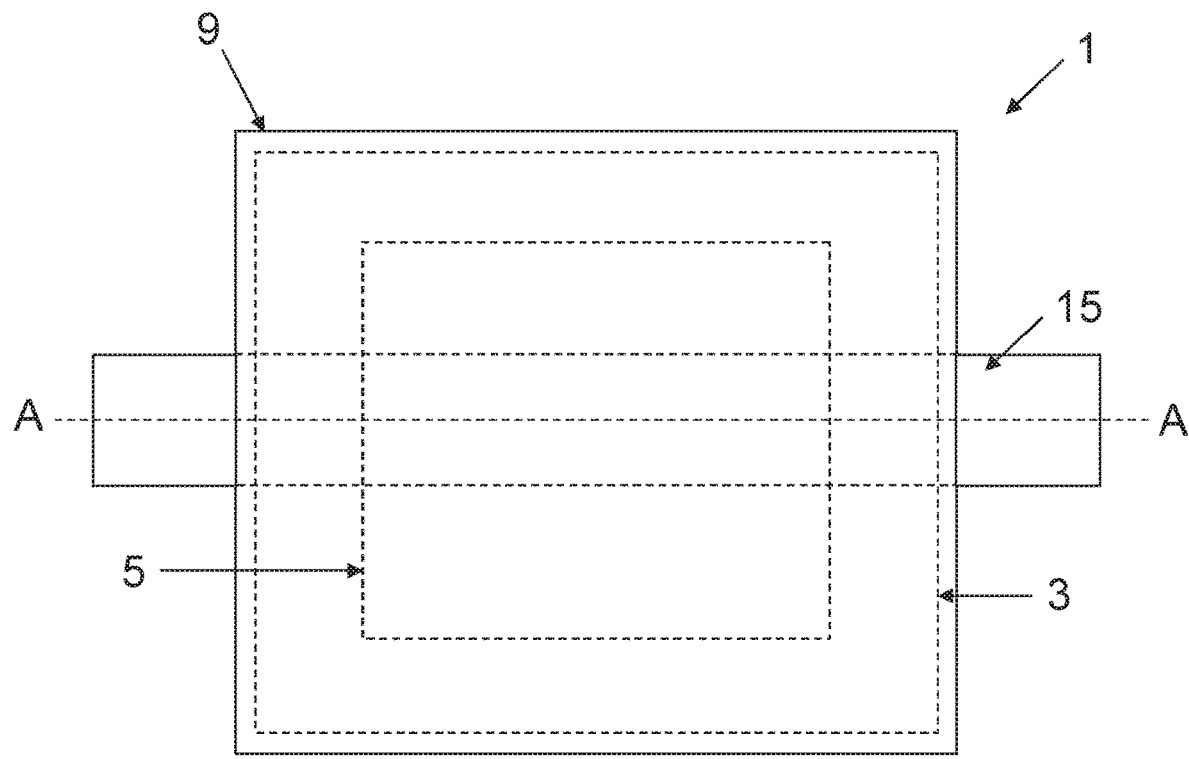
FIG. 3 is a plan view of an article according to an embodiment of the present invention.
Figure 4:
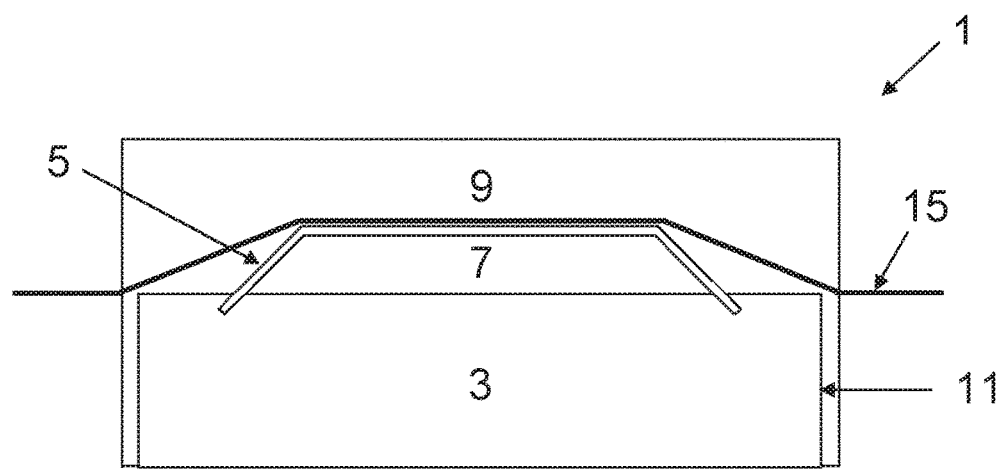
FIG. 4 is a cross-section view taken along the line A-A in FIG. 3.

FIGS. 3 and 4 illustrate a modified embodiment of the present invention in which the device 1 further comprises a section of tape 15. The tape 15 protrudes from two opposite side surfaces of the device 1 and is in contact with an upper surface of the reservoir cover 5. The tape 15 aids attachment of the device 1 on a surface, such as the skin of a person. The tape 15 can be adhered to the surface using a separate adhesive. Although a fluid conduit is not shown in FIGS. 3 and 4 for clarity, a fluid conduit may also be present as in FIGS. 1 and 2.

In other words, the embodiment and the modified embodiment can be combined, so that both the fluid conduit 13 and the tape 15 are present in the article.

When both the fluid conduit 13 and the tape 15 are present, they may be arranged perpendicularly to each other, so that they exit from different side surfaces of the article 1.

The article 1 of the embodiment and the modified embodiment is a pad for positioning on a surface of a patient, typically on the external skin of the patient.

Figure 5:
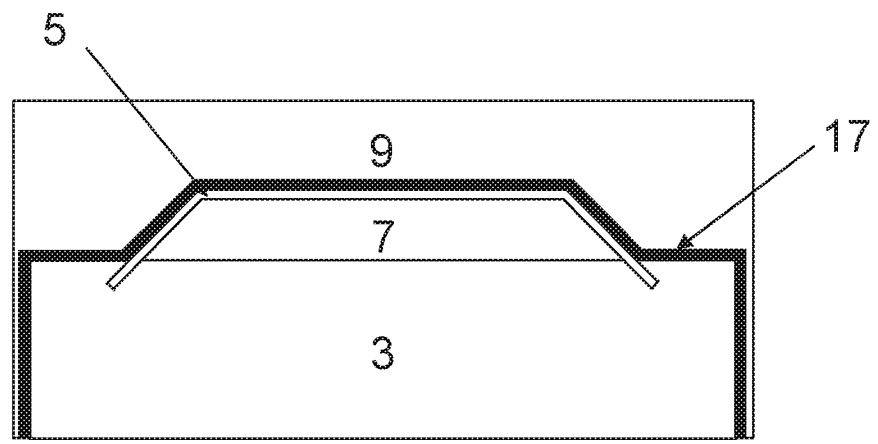
FIG. 5 is a simplified schematic of the cross-section of FIG. 2 or FIG. 4 showing the formation of a skin layer.
Figure 6:
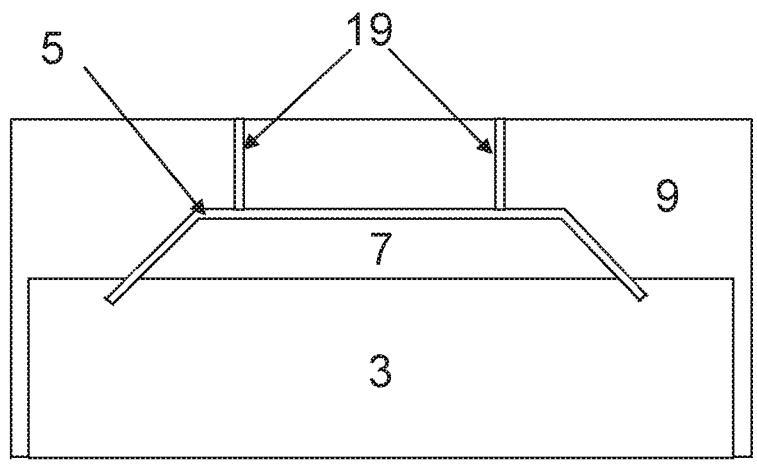
FIG. 6 is a cross-section showing a method of manufacturing an article according to the present invention.

FIG. 5 is a schematic illustration of the article 1 according to the embodiment or the modified embodiment, but with some features omitted for clarity. As shown in FIG. 5, a skin layer 17 that is substantially impermeable to liquid is formed at the interfaces between the hydrophobic foam layer 9 and the reservoir cover 5 and the hydrophilic foam layer 3. No skin layer 17 is formed beneath the reservoir cover 5, because the reservoir cover 5 prevents the hydrophobic foam 9 from entering the reservoir cavity 7 beneath the reservoir cover 5 (as discussed in more detail below in relation to a method of making the article).

Thus, when the reservoir cavity 7 is filled with a liquid (using fluid conduit 13), the liquid in the reservoir cavity 7 is substantially only able to exit the reservoir cavity 7 by passing into the hydrophilic foam layer 3 beneath the reservoir cavity 7.

In particular, the reservoir cover 5 and skin layer 17 form a substantially air-tight or fluid-tight seal around the reservoir cavity 7, apart from the bottom surface of the reservoir cavity 7, so that the fluid can only exit the reservoir cavity 7 into the hydrophilic foam layer 3.

Furthermore, liquid entering the hydrophilic foam layer 3 is substantially only able to exit the hydrophilic foam layer 3 through the bottom surface of the hydrophilic foam layer 3, because of the skin layer 17 formed on the side surfaces of the hydrophilic foam layer 3.

Since the hydrophobic foam layer 9 and hydrophilic foam layer 3 are made of foams, both of these layers are compressible.

Furthermore, in this embodiment the reservoir cover 5 is made from polyvinyl chloride having a thickness of 200 μm. Thus, the reservoir cover 5 is flexible, and can be compressed. Furthermore, this material is impermeable to many liquids.

In use, the article 1 is positioned with the lower surface of the hydrophilic foam layer 3 on a surface of a patient, typically the skin of a patient, with the reservoir cavity 7 containing a liquid to be dispensed on to the skin of the patient.

When the patient, or healthcare professional (doctor or nurse) presses on the upper surface of the hydrophobic foam layer 9, the hydrophobic foam layer 9, the flexible reservoir cover 5 and the hydrophilic foam layer 3 are all compressed. The compression of the reservoir cover 5 reduces the volume of the reservoir cavity 7, and liquid is therefore displaced from the reservoir cavity 7 into the hydrophilic foam layer 3. Compression of the hydrophilic foam layer 3 causes liquid in the hydrophilic foam layer 3 to be dispensed from the lower surface of the hydrophilic foam layer 3 onto the skin of the patient. The skin layer 17 prevents liquid from being erroneously dispensed from the sides or upper surface of the article 1. Thus, the liquid, for example an analgesic medication, can be controllably applied to the skin of the person using the article 1.

In these embodiments, the reservoir cover 5 has a rectangular or square shape when viewed from the upper surface of the article 1 (in plan view).

Different sizes of article 1, with different size reservoir cavities 7, may be provided for different applications/circumstances. For example, three different sizes of the article 1 may be provided.

Typically, the reservoir cavity will have a square shape in plan view with a side length of between 2 and 10 centimetres, depending on the application.

Typical volumes of the reservoir cavity 7 may be between 4 and 36 millilitres.

As shown in FIGS. 2 and 4, the reservoir cover 5 has sloping side walls in contact with the upper surface of the hydrophilic foam layer 3 that are inclined relative to the normal line of the upper surface of the hydrophilic foam layer 3. These sloping side walls improve the compressibility/depressability of the reservoir cover 5, and therefore improve dispensing of the liquid from the reservoir cavity 7. The sloping side walls have an angle of 45 degrees in this embodiment.

In these embodiments, the hydrophilic foam layer 3 comprises a hydrophilic polyurethane foam. More specifically, the hydrophilic foam layer is made from a polyol and isocyanate composition, in which the weight ratio of polyol to isocyanate is from 1:1 to 1.5:1.

In one embodiment, in the polyol and isocyanate composition that forms the hydrophilic foam layer, the polyol comprises butane diol, benzenepropanoic acid, 3,5-bis[1,1-dimethylethyl]-4-hydroxy-C7-9 branched alkyl esters (wherein C7-9 is understood to be a carbon backbone having 7 to 9 carbon atoms in it), glycerine, silicone surfactants and triethylene diamine, and/or the isocyanate comprises diphenylmethane-4,4-diisocyanate and triphenylphosphite.

In these embodiments, the hydrophobic foam layer 9 comprises a hydrophobic polyurethane foam. More specifically, the hydrophobic foam layer is made from a polyol and isocyanate composition in which the weight ratio of polyol to isocyanate is from 2:1 to 2.5:1.

In one embodiment, in the polyol and isocyanate composition that forms the hydrophobic foam layer the polyol comprises 94.8% by weight polyoxyalkylene triols, 1.8% by weight triethanolamine, 0.2% by weight dipropylene glycol, 0.1% by weight triethyldiamine, 0.4% by weight organo-modified polysiloxanes, 2.1% by weight C9-11 alcohol ethoxylate and 0.6% by weight 2 [[2 dimethylamino)ethyl] methylamino] ethanol, and/or the isocyanate comprises 50% to 77% by weight diphenylmethanediisocyanate, isomers and homologues thereof, and 23% to 50% by weight isocyanates that are the reaction product of the polyol with methylenediphenyl diisocyanate.

An example polyol composition is listed below:
Polyoxyalklene triols.
Triethanolamine.
Dipropylene glycol.
Triethydiamine.
Organo-modified polysiloxanes.
C9-11 alcohol ethoxylate.
2-{[2-dimethylamino]ethyl]methylamino}ethanol.
An example isocyanate composition is listed below:
Methylenediphenyl diisocyanate. [MDI].
Homopolymer.

Example compositions for different sizes of the article 1 may be as follows.

Small size (40 mm×40 mm×20 mm):
16.5 grams of polyol.
7.5 grams of isocyanate.
3.8 grams of barium sulphate.
Moulded in a 2 impression tool—above ratio's may be varied 1-2% depending on mould temperature.

Medium size (60 mm×60 mm×20 mm):
15.4 grams of polyol.
7 grams of isocyanate.
3.5 grams of barium sulphate.
Moulded in a 1 impression tool—above ratios may be varied 1-2% depending on mould temperature.

Large size (100 mm×100 mm×20 mm):
49 grams of polyol.
22 grams of isocyanate.
11 grams of barium sulphate.
Moulded in a 1 impression tool—above ratio's may be varied 2-3% depending on mould temperature.

However, where visibility under X-ray is not important, the barium sulphate may be omitted, and the amounts of the other components may be amended accordingly (e.g. in proportion).

The above formulations can form the hydrophobic foam of the present invention.

5905/102—High Density Foam System.
This polyol is a mixture of polyols—
Butane diol.
Benzenepropanoic acid.
3,5-bis [1,1-dimethylethyl]-4-hydroxy.
C7-9 branched alkyl esters [stabilizer].
Glycerine.
Silicone surfactants.
Triethylene diamine.
The Isocyanate is an MDI.
Diphenylmethane—4, 4-diisocyanate—ISO 135/159.
Tri phenyl phosphite—TTP.

This formulation of polyol and isocyanate is that recommended by the manufacturers with the ratio of 100 parts polyol to 81 parts of isocyanate and a 1-3% tolerance to allow a variation in product hardness.

This formulation can provide the hydrophilic/haemophilic foam of the present invention.

Where tape is included in the article 1, as shown in FIGS. 3 and 4, the tape may be X-ray detectable tape that an X-ray detectable thread. A possible specification for such an X-ray detectable tape and thread is as follows:
Yarn decitex—3,800+/−10%.
No of filaments—nominal.
Wrapper Yarn [tpi]—7-10 tpi.
Minimum tenacity—1.9Cn/tex.
Composition by weight—Barium Sulphate minimum 60%—Pharmaceutical Grade.
Cytotoxicity—ISO BS5736.
Acute Systemic Toxicity—ISO BS5736.
Intracutaneous Reactivity—ISO BS5736.
Skin Irritation—ISO BS5736.
Contact Sensitsation—ISO BS5736.
Biocompatability & Toxicity—no adverse comments.

Additional Specifications where the tape is made of cotton:
Warp Yarn: 300 denier Optic White Dyed Yarn 29 ends intermingled.
Weft Yarn: 300 denier Optic White Dyed Yarn 1 end intermingled.
X-ray thread: 2800 denier blue twisted yarn.
Warp density: 75.0 ends per cm.
Weft density: 8.0 courses per cm.

Of course, other suitable compositions are known and can be used for the hydrophilic foam layer 3, hydrophobic foam layer 9 and tape 15.

At its most general, a method of making the article of the present invention comprises; positioning a reservoir cover in contact with a first main surface of a hydrophilic foam layer, so that the reservoir cover encloses a reservoir cavity together with the first main surface of the hydrophilic foam layer, the reservoir cavity being for containing a fluid; and forming a hydrophobic foam layer over the first main surface of the hydrophilic foam layer and the reservoir cover, wherein the method further comprises pressing the reservoir cover towards the first main surface of the hydrophilic foam layer when the hydrophobic foam layer is formed over the first main surface of the hydrophilic foam layer and the reservoir cover.

A typical method of manufacturing the article 1 of the present invention uses a mould, and involves the following steps.

Firstly, a preformed hydrophilic/haemophilic foam layer 3 is positioned in a base of the mould, preferably with a small gap between side edges of the hydrophilic/haemophilic foam layer 3 and inside side surfaces of the base of the mould. The hydrophilic/haemophilic foam layer 3 is made in advance.

Then, an appropriately sized reservoir cover 5 is positioned on top of the upper surface of the hydrophilic/haemophilic foam layer 3 within the mould, so that a reservoir cavity 7 is defined between the upper surface of the hydrophilic/haemophilic foam layer 3 and an inner surface of the reservoir cavity 7.

As shown in FIGS. 1 to 4, the reservoir cover 5 typically has a fluid conduit 13 in the form of a catheter attached thereto that passes through the reservoir cover 5 into the reservoir cavity 7, for supplying fluid into the reservoir cavity 7. The fluid conduit is typically attached to an outside surface of the main face of the reservoir cover 5. The reservoir cover 5 may also have the tape 15 in contact with its outer surface.

A non-polymerised hydrophobic layer comprising a polyol and isocyanate composition is then disposed over the hydrophilic/haemophilic layer within the mould, and therefore also over the reservoir cover 5, fluid conduit 13 and tape 15. The hydrophobic layer may also cover side surfaces of the hydrophilic foam layer 3.

Figure 7:
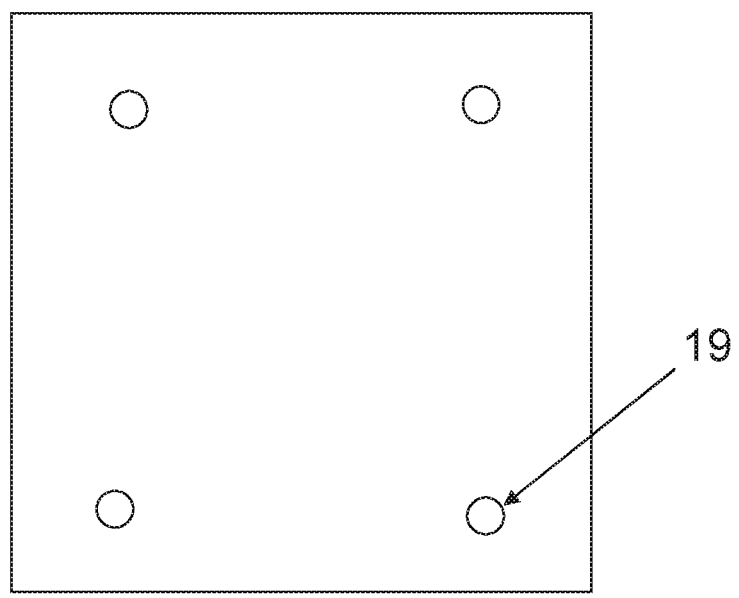
FIG. 7 is a plan view showing a method of manufacturing an article according to the present invention.

At the same time, the reservoir cover 5 is pressed towards the hydrophilic foam layer 3 using a plurality of pins, for example provided in a lid of the mould. FIG. 7 shows an example in which four pins 19 are used to press the reservoir cover 5 down towards the hydrophilic foam layer 3. Where the reservoir cover has a square shape when viewed in plan view, preferably four pins are used to press the reservoir cover towards the hydrophilic foam layer, the four pins contacting the upper surface of the reservoir cover at or adjacent to the corners of the upper surface of the reservoir cover. However, as an alternative, three pins may be used instead, or a different number of pins.

The pressure applied to the reservoir cover 5 by the pins 19 preferably causes the reservoir cover 5 to dig in to (e.g. penetrate) the hydrophilic foam layer 3. Thus, the material of the hydrophobic foam layer 9 is prevented from entering into the reservoir cavity 7.

The hydrophobic layer is then polymerised, to form the article 1.

FIG. 7 shows the locations of four pins used in one embodiment of the present invention. Of course, in other embodiments a different number of pins may be used, and/or the pins may be provided at different positions.

Following this method the skin layer 17 shown in FIG. 5 is formed, and no skin layer is formed below the reservoir cavity 7, so that fluid in the reservoir cavity 7 can exit the reservoir cavity 7 through the lower surface of the reservoir cavity 7 in use of the device.

Of course, in other embodiments different materials may be used for either or both of the foam layers, or for the reservoir cover.

Other aspects and/or embodiments of the present invention are set out in the following numbered clauses:

1. An article comprising:
    a hydrophilic foam layer;
    a reservoir cover in contact with a first main surface of the hydrophilic foam layer, the reservoir cover enclosing a reservoir cavity together with the first main surface of the hydrophilic foam layer, the reservoir cavity being for containing a fluid; and
    a hydrophobic foam layer formed over the first main surface of the hydrophilic foam layer and the reservoir cover.
2. The article according to clause 1, wherein the article is a pad.
3. The article according to clause 1 or clause 2, further comprising a fluid conduit connected to the reservoir cavity for supplying fluid into the reservoir cavity.
4. The article according to clause 3, wherein the fluid conduit is a catheter.
5. The article according to any one of the previous clauses, wherein an edge or edges of the reservoir cover in contact with the first main surface of the hydrophilic form layer are penetrated into the first main surface of the hydrophilic foam layer.
6. The article according to any one of the previous clauses, wherein the reservoir cover is made from a polymer.
7. The article according to any one of the previous clauses, wherein the reservoir cover is made from polyvinyl chloride (PVC).
8. The article according to any one of the previous clauses, wherein the hydrophobic foam layer is further formed on side surfaces of the hydrophilic foam layer.
9. The article according to any one of the previous clauses, wherein a main side of the reservoir cover opposite to the first main surface of the hydrophilic foam layer has a substantially rectangular shape.
10. The article according to clause 9, wherein the main side of the reservoir cover is a square with a side length of between 2 and 10 centimetres.
11. The article according to any one of the previous clauses, wherein a main side of the reservoir cover opposite to the first main surface of the hydrophilic foam layer has a thickness of between 150 µm and 250 µm.
12. The article according to any one of the previous clauses, wherein the reservoir cavity has a volume of between 2 and 40 millilitres.
13. The article according to any one of the previous clauses, wherein the reservoir cover has one or more side walls in contact with the first main surface of the hydrophilic foam layer, wherein the one or more side walls are inclined relative to a normal line of the first main surface.
14. The article according to any one of the previous clauses, wherein the article comprises a tape in contact with an outer surface of the reservoir cover, the tape protruding from a side surface of the article.
15. The article according to clause 14, wherein the tape protrudes from two opposite side surfaces of the article.
16. The article according to any one of the previous clauses, wherein the hydrophilic foam layer comprises a hydrophilic polyurethane foam.
17. The article according to clause 16 wherein the hydrophilic foam layer is made from a polyol and isocyanate composition, in which the weight ratio of polyol to isocyanate is from 1:1 to 1.5:1.
18. The article according to clause 17, wherein, in the polyol and isocyanate composition that forms the hydrophilic foam layer:
    the polyol comprises butane diol, benzenepropanoic acid, 3,5-bis[1,1-dimethylethyl]-4-hydroxy-C7-9 branched alkyl esters (wherein C7-9 is understood to be a carbon backbone having 7 to 9 carbon atoms in it), glycerine, silicone surfactants and triethylene diamine, and/or the isocyanate comprises diphenylmethane-4,4-diisocyanate and triphenylphosphite.
19. The article according to any one of the previous clauses, wherein the hydrophobic foam layer comprises a hydrophobic polyurethane foam.
20. The article according to clauses 19, wherein the hydrophobic foam layer is made from a polyol and isocyanate composition in which the weight ratio of polyol to isocyanate is from 2:1 to 2.5:1.
21. The article according to clause 20, wherein, in the polyol and isocyanate composition that forms the hydrophobic foam layer:
    the polyol comprises 94.8% by weight polyoxyalkylene triols, 1.8% by weight triethanolamine, 0.2% by weight dipropylene glycol, 0.1% by weight triethyldiamine, 0.4% by weight organo-modified polysiloxanes, 2.1% by weight C9-11 alcohol ethoxylate and 0.6% by weight 2 [[2 dimethylamino)ethyl]methylamino] ethanol, and/or
    the isocyanate comprises 50% to 77% by weight diphenylmethanediisocyanate, isomers and homologues thereof, and 23% to 50% by weight isocyanates that are the reaction product of the polyol with methylenediphenyl diisocyanate.
22. The article according to any one of the previous clauses, wherein the article comprises an analgesic fluid in the reservoir cavity.
23. A method of forming an article, the method comprising:
    positioning a reservoir cover in contact with a first main surface of a hydrophilic foam layer, so that the reservoir cover encloses a reservoir cavity together with the first main surface of the hydrophilic foam layer, the reservoir cavity being for containing a fluid; and
    forming a hydrophobic foam layer over the first main surface of the hydrophilic foam layer and the reservoir cover;
    wherein the method further comprises pressing the reservoir cover towards the first main surface of the hydrophilic foam layer when the hydrophobic foam layer is formed over the first main surface of the hydrophilic foam layer and the reservoir cover.

24. The method according to clause 23, wherein the article is an article according to any one of clauses 1 to 22.

25. The method according to clause 23 or clause 24, wherein pressing the reservoir cover towards the first main surface of the hydrophilic foam layer comprises using a pressure applying part to apply pressure to an outer surface of the reservoir cover.

26. The method according to clause 25, wherein the pressure applying part comprises a plurality of pins.

27. The method according to any one of clauses 23 to 26 wherein the method comprises forming the article using a mould.

28. The method according to clause 27 as dependent on clause 25 or clause 26, wherein the pressure applying part is on an internal surface of a lid of the mould.

29. The method according to any one of clauses 23 to 28, wherein the pressing of the reservoir cover towards the first main surface of the hydrophilic foam layer is sufficient to cause an edge or edges of the reservoir cover in contact with the first main surface of the hydrophilic foam layer to penetrate into the first main surface of the hydrophilic foam layer.

The invention claimed is:

1. An article comprising: a hydrophilic foam layer configured to be placed into contact with the skin of a patient; a reservoir cover in contact with a first main surface of the hydrophilic foam layer, the reservoir cover enclosing a reservoir cavity between the reservoir cover and the first main surface of the hydrophilic foam layer, the reservoir cavity being for containing a fluid; and a hydrophobic foam layer formed over the first main surface of the hydrophilic foam layer and the reservoir cover; wherein the reservoir cover has one or more side walls in contact with the first main surface of the hydrophilic foam layer, wherein the one or more side walls are inclined relative to a normal line of the first main surface, and wherein the reservoir cavity is enclosed between a top of the reservoir cover, the side walls of the reservoir cover and the first main surface of the hydrophilic foam layer.

2. The article according to claim 1, wherein the article is a pad.

3. The article according to claim 1, further comprising a fluid conduit connected to the reservoir cavity for supplying fluid into the reservoir cavity.

4. The article according to claim 1, wherein edges of the reservoir cover are in contact with the first main surface of the hydrophilic foam layer, and the edges are penetrated into the first main surface of the hydrophilic foam layer.

5. The article according to claim 1, wherein the reservoir cover is made from a polymer.

6. The article according to claim 1, wherein the hydrophobic foam layer is further formed on side surfaces of the hydrophilic foam layer.

7. The article according to claim 1, wherein a main side of the reservoir cover opposite to the first main surface of the hydrophilic foam layer has a thickness of between 150 μm and 250 μm.

8. The article according to claim 1, wherein the reservoir cavity has a volume of between 2 and 40 millilitres.

9. The article according to claim 1, wherein the article comprises a tape in contact with an outer surface of the reservoir cover, the tape protruding from a side surface of the article.

10. The article according to claim 1, wherein the hydrophilic foam layer comprises a hydrophilic polyurethane foam.

11. The article according to claim 10 wherein the hydrophilic foam layer is made from a polyol and isocyanate composition, in which the weight ratio of polyol to isocyanate is from 1:1 to 1.5:1.

12. The article according to claim 1, wherein the hydrophobic foam layer comprises a hydrophobic polyurethane foam.

13. The article according to claim 12, wherein the hydrophobic foam layer is made from a polyol and isocyanate composition in which the weight ratio of polyol to isocyanate is from 2:1 to 2.5:1.

* * * * *